(12) United States Patent
Stewart et al.

(10) Patent No.: US 8,821,488 B2
(45) Date of Patent: Sep. 2, 2014

(54) TISSUE LESION EVALUATION

(75) Inventors: Mark Stewart, Lino Lakes, MN (US);
David Francischelli, Anoka, MN (US);
Jinback Hong, Maple Grove, MN (US);
Sarah Ahlberg, Crystal, MN (US)

(73) Assignee: Medtronic, Inc., Minneapolis, MN (US)

( * ) Notice: Subject to any disclaimer, the term of this patent is extended or adjusted under 35 U.S.C. 154(b) by 931 days.

(21) Appl. No.: 12/465,435

(22) Filed: May 13, 2009

(65) Prior Publication Data
US 2009/0299365 A1 Dec. 3, 2009

Related U.S. Application Data

(60) Provisional application No. 61/052,742, filed on May 13, 2008.

(51) Int. Cl.
*A61B 18/14* (2006.01)
(52) U.S. Cl.
USPC .............................................. 606/41; 606/52
(58) Field of Classification Search
USPC .............. 606/32, 48, 50, 52, 41; 607/99, 119, 607/102
See application file for complete search history.

(56) References Cited

U.S. PATENT DOCUMENTS

| | | | |
|---|---|---|---|
| 3,736,936 A | 6/1973 | Basiulis et al. | |
| 3,807,403 A | 4/1974 | Stumpf et al. | |
| 3,823,575 A | 7/1974 | Parel | |
| 3,823,718 A | 7/1974 | Tromovitch | |
| 3,827,436 A | 8/1974 | Stumpf et al. | |
| 3,830,239 A | 8/1974 | Stumpf | |
| 3,859,986 A | 1/1975 | Okada et al. | |
| 3,862,627 A | 1/1975 | Hans, Sr. | |
| 3,886,945 A | 6/1975 | Stumpf et al. | |
| 3,907,339 A | 9/1975 | Stumpf et al. | |
| 3,910,277 A | 10/1975 | Zimmer | |
| 3,913,581 A | 10/1975 | Ritson et al. | |
| 3,924,628 A | 12/1975 | Droegemueller et al. | |
| 4,018,227 A | 4/1977 | Wallach | |
| 4,022,215 A | 5/1977 | Benson | |
| 4,061,135 A | 12/1977 | Widran et al. | |
| 4,063,560 A | 12/1977 | Thomas et al. | |
| 4,072,152 A | 2/1978 | Linehan | |
| 4,082,096 A | 4/1978 | Benson | |

(Continued)

OTHER PUBLICATIONS

Chitwood. Wil1C. Sealy, MD: The Father of Arrhythmia Surgery—The Story of the Fisherman with a Fast Pulse. The Annals of Thoracic Surgery 58: 1228-1239, 1994.

(Continued)

*Primary Examiner* — Michael Peffley
*Assistant Examiner* — Thomas Giuliani

(57) ABSTRACT

Device, system and method for ablating tissue of a heart of a patient. The tissue is clamped between a pair of opposing jaws. A portion of the tissue is ablated at a first generally linear position on the tissue by applying ablative energy to two of a plurality of elongate electrodes, each of the two of the plurality of elongate electrodes being coupled in opposing relationship to each other and the pair of opposing jaws, respectively. An effectiveness of the ablation is sensed at a second generally linear position on the tissue with at least one of the plurality of elongate electrodes positioned on one of the pair of opposing jaws. The second linear position on the tissue is laterally distal to the first linear position on the tissue with respect to the atrium of the heart.

16 Claims, 8 Drawing Sheets

(56) References Cited

U.S. PATENT DOCUMENTS

| | | |
|---|---|---|
| 4,207,897 A | 6/1980 | Lloyd et al. |
| 4,248,224 A | 2/1981 | Jones |
| 4,275,734 A | 6/1981 | Mitchiner |
| 4,278,090 A | 7/1981 | van Gerven |
| 4,377,168 A | 3/1983 | Rzasa et al. |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,936,281 A | 6/1990 | Stasz |
| 4,946,460 A | 8/1990 | Merry et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelna |
| 5,100,388 A | 3/1992 | Behl et al. |
| 5,108,390 A | 4/1992 | Potocky et al. |
| 5,147,355 A | 9/1992 | Friedman et al. |
| 5,178,133 A | 1/1993 | Pena |
| 5,207,674 A | 5/1993 | Hamilton |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,254,116 A | 10/1993 | Baust et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,334,181 A | 8/1994 | Rubinsky et al. |
| 5,334,193 A | 8/1994 | Nardella |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,385,148 A | 1/1995 | Lesh et al. |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,423,807 A | 6/1995 | Milder |
| 5,423,811 A | 6/1995 | Imran et al. |
| 5,427,119 A | 6/1995 | Swartz et al. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,443,463 A | 8/1995 | Stern et al. |
| 5,443,470 A | 8/1995 | Stern et al. |
| 5,450,843 A | 9/1995 | Moll et al. |
| 5,452,582 A | 9/1995 | Longsworth |
| 5,452,733 A | 9/1995 | Sterman et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,558,671 A | 9/1996 | Yates |
| 5,560,362 A | 10/1996 | Silwa, Jr. et al. |
| 5,562,720 A | 10/1996 | Stern et al. |
| 5,569,241 A | 10/1996 | Edwards |
| 5,571,088 A | 11/1996 | Lennox et al. |
| 5,571,215 A | 11/1996 | Sterman et al. |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,607,462 A | 3/1997 | Imran |
| 5,617,854 A | 4/1997 | Munsif |
| 5,630,837 A | 5/1997 | Crowley |
| 5,637,090 A | 6/1997 | McGee et al. |
| 5,643,197 A | 7/1997 | Brucker et al. |
| 5,656,029 A | 8/1997 | Imran et al. |
| 5,658,278 A | 8/1997 | Imran et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |
| 5,681,278 A | 10/1997 | Igo et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,713,942 A | 2/1998 | Stern et al. |
| 5,716,389 A | 2/1998 | Walinsky et al. |
| 5,718,241 A | 2/1998 | Ben-Haim et al. |
| 5,718,701 A | 2/1998 | Shai et al. |
| 5,720,775 A | 2/1998 | Larnard |
| 5,722,402 A | 3/1998 | Swanson et al. |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,735,280 A | 4/1998 | Sherman et al. |
| 5,735,290 A | 4/1998 | Sterman et al. |
| 5,755,760 A | 5/1998 | Maguire et al. |

(56) References Cited

U.S. PATENT DOCUMENTS

| | | |
|---|---|---|
| 5,769,846 A | 6/1998 | Edwards et al. |
| 5,782,828 A | 7/1998 | Chen et al. |
| 5,785,706 A | 7/1998 | Bednarek |
| 5,788,636 A | 8/1998 | Curley |
| 5,792,140 A | 8/1998 | Tu et al. |
| 5,797,960 A | 8/1998 | Stevens et al. |
| 5,800,428 A | 9/1998 | Nelson et al. |
| 5,800,482 A | 9/1998 | Pomeranz et al. |
| 5,810,802 A | 9/1998 | Panescu et al. |
| 5,827,216 A | 10/1998 | Igo et al. |
| 5,836,947 A | 11/1998 | Fleischman et al. |
| 5,840,030 A | 11/1998 | Ferek-Petric et al. |
| 5,844,349 A | 12/1998 | Oakley et al. |
| 5,846,187 A | 12/1998 | Wells et al. |
| 5,846,191 A | 12/1998 | Wells et al. |
| 5,849,028 A | 12/1998 | Chen |
| 5,871,523 A | 2/1999 | Fleischman et al. |
| 5,871,525 A | 2/1999 | Edwards et al. |
| 5,873,845 A | 2/1999 | Cline et al. |
| 5,876,399 A | 3/1999 | Chia et al. |
| 5,879,295 A | 3/1999 | Li et al. |
| 5,879,296 A | 3/1999 | Ockuly et al. |
| 5,881,732 A | 3/1999 | Sung et al. |
| 5,882,346 A | 3/1999 | Pomeranz et al. |
| 5,885,278 A | 3/1999 | Fleischman |
| 5,893,848 A | 4/1999 | Negus et al. |
| 5,895,417 A | 4/1999 | Pomeranz et al. |
| 5,897,553 A | 4/1999 | Mulier |
| 5,897,554 A | 4/1999 | Chia et al. |
| 5,899,898 A | 5/1999 | Arless et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,927,284 A | 7/1999 | Borst et al. |
| 5,928,191 A | 7/1999 | Houser et al. |
| 5,931,810 A | 8/1999 | Grabek |
| 5,931,848 A | 8/1999 | Saadat |
| 5,954,661 A | 9/1999 | Greenspon et al. |
| 5,971,980 A | 10/1999 | Sherman |
| 5,971,983 A | 10/1999 | Lesh |
| 5,993,447 A | 11/1999 | Blewett et al. |
| 6,007,499 A | 12/1999 | Martin et al. |
| 6,012,457 A | 1/2000 | Lesh |
| 6,016,811 A | 1/2000 | Knopp et al. |
| 6,042,556 A | 3/2000 | Beach et al. |
| 6,063,081 A | 5/2000 | Mulier |
| 6,071,279 A | 6/2000 | Whayne et al. |
| 6,088,894 A | 7/2000 | Oakley |
| 6,096,037 A | 8/2000 | Mulier |
| 6,113,592 A | 9/2000 | Taylor |
| 6,117,101 A | 9/2000 | Diederich et al. |
| 6,120,496 A | 9/2000 | Whayne et al. |
| 6,142,993 A | 11/2000 | Whayne et al. |
| 6,142,994 A | 11/2000 | Swanson et al. |
| 6,152,920 A | 11/2000 | Thompson et al. |
| 6,161,543 A | 12/2000 | Cox et al. |
| 6,165,174 A | 12/2000 | Jacobs et al. |
| 6,217,528 B1 | 4/2001 | Koblish et al. |
| 6,217,576 B1 | 4/2001 | Tu et al. |
| 6,224,592 B1 | 5/2001 | Eggers et al. |
| 6,231,518 B1 | 5/2001 | Grabek et al. |
| 6,235,024 B1 | 5/2001 | Tu |
| 6,237,605 B1 | 5/2001 | Vaska et al. |
| 6,238,347 B1 | 5/2001 | Nix et al. |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,128 B1 | 6/2001 | Knopp et al. |
| 6,270,471 B1 | 8/2001 | Hechel et al. |
| 6,293,943 B1 | 9/2001 | Panescu et al. |
| 6,296,619 B1 | 10/2001 | Brisken et al. |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,325,797 B1 | 12/2001 | Stewart et al. |
| 6,328,736 B1 | 12/2001 | Mulier |
| 6,332,881 B1 | 12/2001 | Carner et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey et al. |
| 6,413,254 B1 | 7/2002 | Hissong et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,956 B1 | 10/2002 | Hsuan et al. |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,484,727 B1 | 11/2002 | Vaska et al. |
| 6,488,680 B1 | 12/2002 | Francischelli |
| 6,502,575 B1 | 1/2003 | Jacobs et al. |
| 6,514,250 B1 | 2/2003 | Jahns |
| 6,527,767 B2 | 3/2003 | Wang et al. |
| 6,537,248 B2 | 3/2003 | Mulier |
| 6,537,272 B2 | 3/2003 | Christopherson et al. |
| 6,558,382 B2 | 5/2003 | Jahns |
| 6,584,360 B2 | 6/2003 | Francischelli |
| 6,585,732 B2 | 7/2003 | Mulier |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,645,199 B1 | 11/2003 | Jenkins et al. |
| 6,648,883 B2 | 11/2003 | Francischelli |
| 6,656,175 B2 | 12/2003 | Francischelli |
| 6,663,627 B2 | 12/2003 | Francischelli |
| 6,692,450 B1 | 2/2004 | Coleman |
| 6,699,240 B2 | 3/2004 | Francischelli |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,807,968 B2 | 10/2004 | Francischelli |
| 6,827,715 B2 | 12/2004 | Francischelli |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,916,318 B2 | 7/2005 | Francischelli |
| 6,949,097 B2 | 9/2005 | Stewart et al. |
| 6,960,205 B2 | 11/2005 | Jahns |
| 6,962,589 B2 | 11/2005 | Mulier |
| 2003/0004507 A1* | 1/2003 | Francischelli et al. ......... 606/41 |

(56) References Cited

U.S. PATENT DOCUMENTS

| | | | |
|---|---|---|---|
| 2003/0018329 A1* | 1/2003 | Hooven | 606/41 |
| 2004/0082948 A1 | 4/2004 | Stewart et al. | |
| 2005/0010095 A1 | 1/2005 | Stewart et al. | |
| 2005/0119653 A1* | 6/2005 | Swanson | 606/49 |

OTHER PUBLICATIONS

Gallagher et al. Cryosurgical Ablation of Accessory Atrioventrical Connections: A Method for Correction of the Pre-excitation Syndrome. Circulation 55(3): 471-479, 1977.

Sealy. Direct Surgical Treatment of Arrhythmias: The Last Frontier in Surgical Cardiology. Chest 75(5): 536-537, 1979.

Sealy. The Evolution of the Surgical Methods for Interruption of Right Free Wall Kent Bundles. The Annals of Thoracic Surgery 36(1): 29-36, 1983.

Guiraudon et al. Surgical Repair of Wolff-Parkinson-White Syndrome: A New Closed-Heart Techique. The Annals of Thoracic Surgery 37(1): 67-71, 1984.

Klein et al. Surgical Correction of the Wolff-Parkinson-White Syndrome in the Closed Heart Using Cryosurgery: A Simplified Approach. JACC 3(2): 405-409, 1984.

Randall et al. Local Epicardial Chemical Ablation of Vagal Input to Sino-Atrial and Atrioventricular Regions of the Canine Heart. Journal of the Autonomic Nervous System 11:145-159, 1984.

Guiraudon et al. Surgical Ablation of Posterior Septal Accessory Pathways in the Wolf-Parkinson-White Syndrome by a Closed Heart Technique. Journal Thoracic Cardiovascular Surgery 92:406-413, 1986.

Gallagher et al. Surgical Treatment of Arrhythmias. The American Journal of Cardiology 61:27A-44A, 1988.

Mahomed et al. Surgical Division of Wolff-Parkinson-White Pathways Utilizing the Closed-Heart Technique: A 2-Year Experience in 47 Patients. The Annals of Thoracic Surgery 45(5): 495-504, 1988.

Cox et al. Surgery for Atrial Fibrillation; Seminars in Thoracic and Cardiovascular Surgery, vol. 1, No. 1 (Jul. 1989) pp. 67-73.

Bredikis et al; Surgery of Tachyarrhythmia: Intracardiac Closed Heart Cryoablation; PACE, vol. 13, pp. 1980-1984.

McCarthy et al. Combined Treatment of Mitral Regurgitation and Atrial Fibrillation with Valvuloplasty and the Maze Procedure. The American Journal of Cardiology 71: 483-486, 1993.

Yamauchi et al. Use of Intraoperative Mapping to Optimize Surgical Ablation of Atrial Flutter. The Annals of Thoracic Surgery 56: 337-342, 1993.

Graffigna et al. Surgical Treatment of Wolff-Parkinson-White Syndrome: Epicardial Approach Without the Use of Cardiopulmonary Bypass. Journal of Cardiac Surgery 8: 108-116, 1993.

Surgical treatment of atrial fibrillation: a review; Europace (2004) 5, S20-S29.

Elvan et al. Radiofrequency Catheter Ablation of the Atria Reduces Inducibility and Duration of Atrial Fibrillation in Dogs. Circulation 91: 2235-2244, 1995.

Cox et al. Modification of the Maze Procedure for Atrial Flutter and Atrial Fibrillation. I. Rational and Surgical Results. The Journal of Thoracic Cardiovascular Surgery 110: 473-484, 1995.

Cox, The Maze III Procedure for Treatment of Atrial Fibrillation. Sabiston DC, ed Atlas of Cardiothoracic Surgery, Philadelphia: WB Saunders: 460-475, 1994.

Sueda et al. Simple Left Atrial Procedure for Chronic Atrial Fibrillation Associated with Mitral Valve Disease. The Annals of Thoracic Surgery 62(6): 1796-1800, 1996.

Tsui et al. Maze 3 for Atrial Fibrillation: Two Cuts Too Few? PACE 17: 2163-2166, 1994.

Kosakai et al. Cox Maze Procedure for Chronic Atrial Fibrillation Associated with Mitral Valve Disease. The Journal of Thoracic Cardiovascular Surgery 108: 1049-1055, 1994.

Cox et al., "The Surgical Treatment of Atrial Fibrillation, IV Surgical Technique," *J of Thorac Cardiovasc Surg*, 1991: 101: 584-593.

Nardella, Radio Frequency Energy and Impedance Feedback, SPIE vol. 1068, Catheter Based Sensing and Imaging Technology (1989).

Avitall Et. Al., "A Thoracoscopic Approach to Ablate Atrial Fibrillation Via Linear Radiofrequency Lesion Generation on the Epicardium of Both Atria," PACE, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:450,I-675,#3946.

Sie et al., "Radiofrequency Ablation of Atrial Fibrillation in Patients Undergoing Valve Surgery," Circulation (Nov. 1997) 84:1450,#2519.

Jais et al., "Catheter Ablation for Paroxysmal Atrial Fibrillation: High Success Rates with Ablation in the Left Atrium," Circulation (Nov. 1996) 94:I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Supp 1):I-493, #2889.

Cox et al., "An 8 1/2 Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Simple Left Atrial Procedure for Chronic Atrial Fibrillation Associated with Mitral Valve Disease," Ann Thorac Surg, 1996;62:1796-1800.

Sueda et al., "Efficacy of a Simple Left Atrial Procedure for Chronic Atrial Fibrillation in Mitral Valve Operations," Ann Thorac Surg, 1997;63:1070-1075.

* cited by examiner

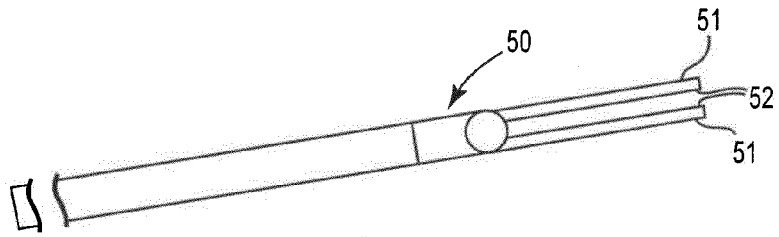
Fig. 2
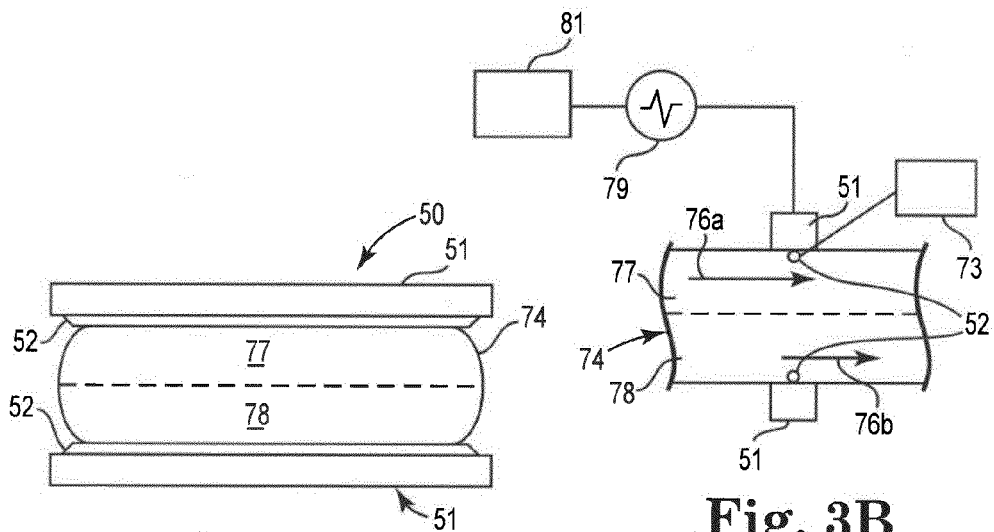
Fig. 3A
Fig. 3B
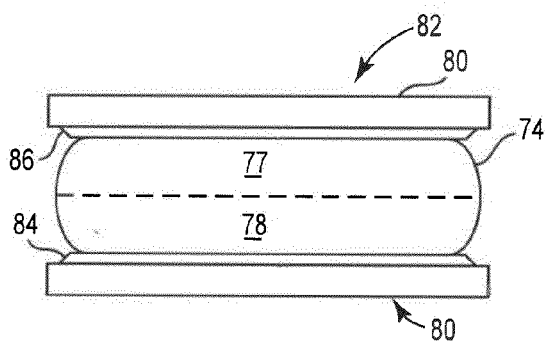
Fig. 4A
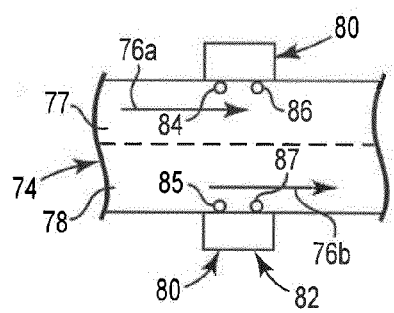
Fig. 4B

TISSUE LESION EVALUATION

RELATED APPLICATION

This application claims the benefit under 35 U.S.C. §119 (e) of U.S. Patent application Ser. No. 61/052,742, filed May 13, 2008, which is herein incorporated by reference in its entirety.

FIELD

This disclosure relates to the evaluation of the effectiveness of surgically created lesions in tissue, in particular, cardiac tissue. In one particular example, this disclosure relates to improved tools and methods used to determine the effectiveness of surgically created lesions intended to reduce or eliminate atrial fibrillation.

BACKGROUND

In certain people at certain times, electrical signals within heart tissue may not function properly and can create cardiac arrhythmias. Ablation of cardiac conduction pathways in the region of tissue where the signals are malfunctioning may reduce or eliminate such faulty signals. Ablation involves creating lesions on tissue during surgery. To provide effective therapy, surgically created lesions may block the transmission of cardiac contractions.

Ablation may be accomplished in several ways. Sometimes ablation is necessary only at discrete positions along the tissue, is the case, for example, when ablating accessory pathways, such as in Wolff-Parkinson-White syndrome or AV nodal reentrant tachycardias. At other times, however, ablation is desired along a line (either straight or curved), called linear ablation. (In contrast to linear ablation, ablations at discrete positions along the tissue are called non-linear or focal ablations.) One way is to position a tip portion of the ablation device so that an ablation electrode is located at one end of the target site, which may be a lesion line. Then energy is applied to the electrode to ablate the tissue adjacent to the electrode. The tip portion of the electrode is then dragged or slid along the length of the desired lesion line while delivering energy. A second way of accomplishing linear ablation is to use an ablation device having a series of spaced-apart band or coil electrodes that, after the electrode portion of the ablation device has been properly positioned, are energized simultaneously or one at a time to create the desired lesion. If the electrodes are close enough together the lesions run together sufficiently to create a continuous linear lesion.

Typical areas of the heart that are treated using surgically created continuous linear lesions are located in the atria. This may be the case for atrial fibrillation, which is a common form of arrhythmia. The aim of linear ablation in the treatment of atrial fibrillation may be to reduce the total mass of electrically connected atrial tissue below a threshold believed to be needed for sustaining multiple reentry wavelets. Linear transmural lesions may be created between electrically non-conductive anatomic landmarks to reduce the contiguous atrial mass. Transmurality is achieved when the full thickness of the target tissue is ablated.

In a procedure to treat atrial fibrillation, the pulmonary vein ostia may be isolated on a beating heart from the left atrium using a linear bipolar ablation clamp device. The linear clamp device often delivers radio frequency energy between the linear electrodes, which may heat and kill the portion of myocardium that is clamped between the two electrodes. This may form a continuous line of inactive myocardium encircling that portion of the heart. With this method, all tissue distal to, or away from, the heart may be isolated from the normal heart contractile function.

Before the procedure is complete, the area of the heart may be tested to confirm a conduction block or see if the ablation is effective and eliminates the undesired electrical signals. Present methods to confirm conduction block include the use of electrophysiology catheters to evaluate pulmonary vein isolation lesions and monopolar and bipolar focal probes using pacing or electrogram techniques, and are described below.

Surgeons may use multi-polar electrophysiology catheters to evaluate pulmonary vein isolation by manually placing the catheters on the lesion or on one side or the other of the lesion. The catheters may be used to provide information that will display bipolar electrograms from electrode pairs on the catheters for analysis. This can be done using an electrophysiology recording system or a portable pacemaker programmer/analyzer. In these cases, the surgeon removes the ablation device from the patient and then replaces it with the catheters or the probes. This can be cumbersome in that medical professionals may prefer the simplicity of a single surgical instrument with which to perform both ablation and lesion evaluations whenever possible.

Additionally, procedures on a beating heart may be preferred over procedures on an arrested or stopped heart. Holding a catheter designed for endocardial use on the epicardial surface in a stable location on a beating heart may be challenging. The catheters may be held against the epicardial surface with forceps where the surgeon provides a force to keep the catheter steady against the beating heart. In addition to having to maintain a constant position placement of the catheter, the catheter can be misplaced. Only the active myocardium below each pair of electrodes may be detected. If the electrodes are not positioned correctly, the results can falsely indicate that isolation has been achieved. In the same way, pacing can be used from an electrode pair to evaluate if there is an effective conduction block.

In addition to the catheters, probe-type devices can be used to evaluate cardiac conduction block using pacing or local electrogram sensing techniques. For example, a monopolar pacing device can be used to evaluate conduction block by placing a ground electrode needle into the intercostal muscle of the chest, which is also connected to the positive pole of the pacing pulse generator. A detector probe may be connected to the negative pole of the pacing pulse generator. The detector probe can be used to apply pacing stimuli to discrete locations within a region of tissue isolated from the ablation. The region can be considered isolated if pacing from the region does not produce ventricular capture. Failure to capture the tissue under the probe tip, however, could also be due to a lack of myocardium in that specific area. In addition, myocardium could be present and remain undetected in other adjacent areas within the areas intended for isolation. Thus, even though the probe may appear to be positioned properly, if it is not positioned directly adjacent to a portion of the lesion that failed to create a complete block, the probe may fail to register the existence of the incomplete lesion. This is because while the portion of the lesion it is adjacent to may be complete, other portions of the lesion may not be complete.

Other probes may be designed for monopolar and bipolar focal ablation and also bipolar pacing and electrogram sensing. In a similar way to the above-described bipolar probe, the probes may not cover much area on the tissue as they detect or stimulate active non-isolated myocardium. Probes may be placed on the myocardium that connects to the atrium to improve the likelihood that tissue adjacent to the probe is connected to the atrium. Thus, the probe may be moved over many portions of the isolated tissue to determine that no isolated regions exist. Further, the probes might not be the preferred ablation device of the medical professional, and so the selected ablation device may be removed and replaced with a new sensing tool, similar to the cumbersome procedures described above with the electrophysiology catheters.

SUMMARY

While medical professionals have developed methods which may mitigate the likelihood of a non-elongate probe missing an incomplete lesion by prescribing moving the probe and testing at many different locations, such methods may be time consuming. An ablation device has been developed with elongate, generally linear electrodes which may be utilized both in ablating tissue and in sensing for complete entry or exit block by being repositioned once to a spot distal of the ablation location relative to the heart and sensing. While in the past it may have been thought that elongate electrodes may not be effective at sensing and pacing, devices and methods have been developed which may enable elongate electrodes to be effective in sensing and pacing.

Moreover, additional embodiments of the ablation device may incorporate more than two elongate electrodes, spaced apart so that the ablation device need not be repositioned in order to first ablate the tissue, then sense and pace the tissue in order to determine the effectiveness of the ablation procedure. In addition, research into the impact of the force of electrodes on the tissue during sensing and pacing has suggested that while it may be advantageous to deliver ablation energy while using a relatively strong clamping force, it may be advantageous to sense and pace using a relatively weak force. Accordingly, ablation energy and sensing and pacing may incorporate different clamping forces. Similarly, while it may be desirable to utilize relatively large amounts of conductive fluid during ablation, it may be desirable to limit the amounts of conductive fluid during sensing and pacing. Accordingly, fluid delivery may be managed based on whether the ablation device is delivering ablation energy or sensing or pacing.

In an embodiment, a method is disclosed for ablating tissue of a heart having an atrium. The tissue is clamped between a pair of opposing jaws. A portion of the tissue is ablated at a first generally linear position on the tissue by applying ablative energy to two of a plurality of elongate electrodes, each of the two of the plurality of elongate electrodes being coupled in opposing relationship to each other and the pair of opposing jaws, respectively. Then an effectiveness of ablation on the portion of the tissue at a second generally linear position on the tissue is sensed with at least one of the plurality of elongate electrodes positioned on one of the pair of opposing jaws. The second linear position on the tissue are laterally distal to the first linear position on the tissue with respect to the atrium.

In an embodiment, the plurality of elongate electrodes are a pair of elongate electrodes.

In an embodiment, after the ablating step, the pair of opposing jaws are repositioned to the second generally linear position.

In an embodiment, the plurality of elongate electrodes are at least three electrodes, and the ablating step ablates with a first two of the plurality of elongate electrodes of the sensing step senses with a third one of the plurality of elongate electrodes.

In an embodiment, the plurality of elongate electrodes are four electrodes, the ablating step ablates the tissue with a first two electrodes of the plurality of elongate electrodes, and the sensing step senses an effectiveness of ablation with a second two electrodes of the plurality of elongate electrodes. Each of the second two of the plurality of elongate electrodes are coupled in opposing relationship to each other and the pair of opposing jaws, respectively.

In an embodiment, the two electrodes of the sensing step are positioned generally parallel to the two electrodes of the ablating step.

In an embodiment, the clamping step comprises clamping the tissue between the jaws with a first clamping force, and further comprising the step, after the ablating step and before the sensing step of clamping the tissue between the jaws with a second clamping force, the first clamping force being greater than the second clamping force, without repositioning the jaws.

In an embodiment, the clamping step comprises clamping the tissue between the jaws with a first clamping force, and further comprising the step, after the ablating step and before the sensing step of clamping the tissue between the jaws at the second linear position with a second clamping force, the first clamping force being greater than the second clamping force.

In an embodiment, the jaws are fluidly coupled to a fluid supply of a fluid, and during the ablating step a first amount of the fluid is delivered to the jaws. During the sensing step a second amount of the fluid is delivered to the jaws, the first amount of fluid being greater than the second amount of fluid.

In an embodiment, the first amount and the second amount are a first total volume of the fluid and a second total volume of the fluid, respectively.

In an embodiment, the first amount and the second amount are a first rate of delivery of the fluid and a second rate of the fluid, respectively.

In an embodiment, sensing comprises a first test and a second test.

In an embodiment, the first test senses cardiac muscle cell depolarization.

In an embodiment, at least one of the plurality of elongate electrodes is coupled to a source of pacing energy and the test comprises delivering the pacing energy and detecting a response of the heart to the pacing energy.

In an embodiment, sensing uses two of the plurality of electrodes.

In an embodiment, the heart has a right pulmonary vein having a width and a left pulmonary vein having a width, and the first generally linear position spans the width of at least one of the right pulmonary vein and the left pulmonary vein.

In an embodiment, the second generally linear position spans a width of the at least one of the right pulmonary vein and the left pulmonary vein distal of the first generally linear position relative to the atrium.

In an embodiment, system is disclosed for ablating tissue of a heart having an atrium. The system has a set of opposing jaws movably coupled with respect to each other and a plurality of opposing elongate electrodes positioned with respect to the set of jaws. The system also has a source of ablation energy coupled to two opposing ones of the plurality of elongate electrodes and delivering ablation energy to the tissue to form a lesion and a sensing module coupled to at least one of the plurality of elongate electrodes which senses a completeness of the lesion.

In an embodiment, the system as has a clamp force regulator which regulates a clamping force on the tissue by the set of jaws.

In an embodiment, the clamp force regulator regulates the clamping force to a first clamping force and a second clamping force.

In an embodiment, the first clamping force is greater than the second clamping force.

In an embodiment, the system also has a fluid supply containing a fluid, the fluid supply being fluidly coupled to the jaws to deliver a first amount of the fluid corresponding to the source of ablation energy delivering the ablation energy and a second amount of fluid corresponding to the sensing module sensing a completeness of the lesion.

In an embodiment, the heart has a right pulmonary vein having a width and a left pulmonary vein having a width, and each of the plurality of opposing elongate electrodes spans the width of at least one of the right pulmonary vein and the left pulmonary vein.

In an embodiment, an ablation device has a set of opposing jaws movably coupled with respect to each other, a first pair of opposing elongate electrodes positioned with respect to the set of jaws, and a second pair of opposing elongate electrodes positioned with respect to the set of jaws and generally adjacent and parallel to the first pair of opposing elongate electrodes.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 2 illustrates a schematic view of a device constructed in accordance with the present disclosure;

FIGS. 3A and 3B illustrate an example of the device of FIG. 2;

FIGS. 4A and 4B illustrate another example of the device of FIG. 2;

DESCRIPTION

Figure 1A:
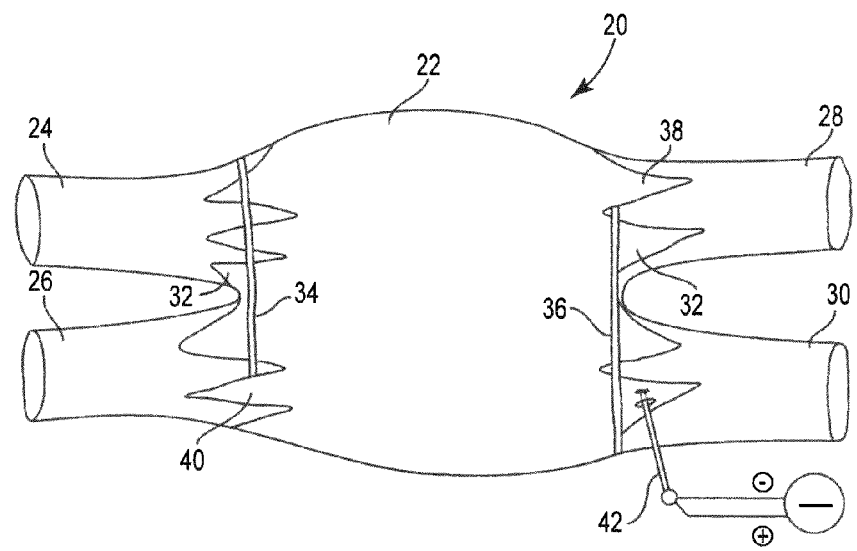
FIGS. 1A and 1B are schematic drawings of a heart with incomplete surgically created lesions.
Figure 1B:
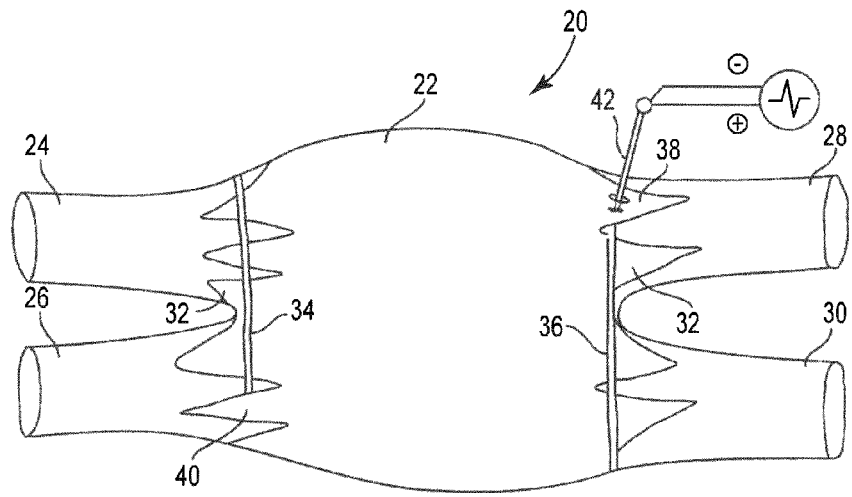

FIGS. 1A and 1B illustrate a portion of heart 20 as viewed from facing the back of a patient. The portion of heart 20 includes left atrial myocardium 22, left superior pulmonary vein 24, left inferior pulmonary vein 26, right superior pulmonary vein 28 and right inferior pulmonary vein 30. Newly oxygenated blood returns from the lungs into the left atrium through right and left pulmonary veins 24,26,28,30. The Figures also illustrate left atrial myocardium and myocardial extensions 32 onto pulmonary veins 24,26,28,30. In order to treat atrial fibrillation, transmural lesion 34 may be formed on the left atrium proximal to left pulmonary veins 24, 26 and transmural lesion 36 may be formed on the left atrium proximal to right pulmonary veins 28, 30. In alternative embodiments, transmural lesion 34 may be formed on the left atrium, proximate left pulmonary veins 24, 26, and transmural lesion 36 may be formed on the left atrium proximate right pulmonary veins 28, 30. As illustrated, lesions 34, 36 are incomplete. An incomplete lesion 36 allows an unablated and thus active muscle extension, or sleeve 38, in the right superior pulmonary vein 28 to connect with the left atrium 22. Also, incomplete lesion 34 allows an unablated muscle extension, or sleeve, 40 in left inferior pulmonary vein 26 to connect with the atrium 22.

Evaluating conduction block can be performed with two methods, entrance block and exit block. Entrance block involves verification that there are no local electrogram signals detected on the intended isolated side of the lesion. If electrogram signals are detected on the intended isolated side, then isolation may not have been achieved. Exit block involves pacing tissue within the intended isolated side to determine whether the activation leaves or exits the intended isolated region. If the activation does exit the intended isolated region, then isolation may not have been achieved.

FIGS. 1A and 1B illustrate the difficulties of detecting incomplete lesions on ablated tissues of heart 20 designed to treat atrial fibrillation. FIG. 1A illustrates a bipolar probe 42 placed on an isolated portion of muscle 32. Pacing stimulation at this location 32 would not pace heart 20 and would not detect active muscle fiber 38. This may result in falsely concluding right pulmonary veins 28, 30 are fully isolated or repeating the test on several other locations of right pulmonary veins 28, 30. FIG. 1B illustrates bipolar probe 42 placed on non isolated sleeve 38. Pacing stimulation at this location 38 would pace heart 20 and an electrogram would be detected. This would indicate a lack of electrode block on right pulmonary veins 28, 30. Similar results can be achieved by point pacing left pulmonary veins 24, 26.

FIG. 2 illustrates bipolar ablation device 50 having a pair of opposing jaws 51, each having elongate linear ablation electrodes 52, which may be "full length," in opposition to each other. Opposing jaws 51 are configured to be clamped together on tissue, e.g., cardiac tissue, during surgery. Full length linear ablation electrodes 52 have a length larger than a length of point probes and are effective in performing functions of this disclosure. Bipolar ablation device 50 and electrodes 52 may be used to ablate tissue to create lesions 34, 36 as well as evaluate lesions 34, 36 by sensing the effectiveness of the ablation, for example by pacing tissue and sensing a response without having to use a separate device. Elongate electrodes 52 may be straight or have curves to conform to the anatomy of the patient. In an embodiment, electrodes 52 may have curves while remaining generally linear. In alternative embodiments, electrodes 52 are straight.

In one embodiment, bipolar electrodes 52 are used to create lesion 34, 36 at a first generally linear position. Then jaws 51 are moved to a second generally linear position on the tissue distal of lesion 34, 36 relative to the atria and placed against the tissue for sensing effectiveness of ablation by determining isolation. Jaws 51 can be moved very soon after ablating to test isolation. The use of the elongate ablation electrodes 52 to evaluate a conduction block allows detection of small areas of myocardium that could be missed if discrete electrodes such as probes were used, such as indicated in FIG. 1A. Further, the elongate electrodes 52 may be able to detect and integrate any discrete areas of cardiac activity along the length of electrodes 52 so an electrogram may be detected if there is any cardiac muscle contractile activity along the length of electrodes 52. Jaws 51 may be moved distal to the atria from the lesion site to measure the tissue for electrograms to determine entrance block and to pace heart 20 from jaws 51 to determine exit block.

Ablation generator 73 is electrically coupled to bipolar electrodes 52 to provide a source of ablation energy. Further, sensing module 79 may be electrically coupled to electrodes 52 in order to allow electrogram collection for sensing the effectiveness of ablation in conventional manner. Further, electrodes 52 can be coupled to a radiofrequency (RF) filtered device such that pacing and electrogram collection can be performed during ablation of the tissue site being ablated. Pacing and electrogram collection while ablating tissue can be used to determine an effectiveness of ablation when tissue distal to and, in an embodiment, within the lesion line becomes at least partially electrically isolated and disconnected from the atrial chamber.

An irrigation fluid may be delivered to jaws 51 and may be any suitable fluid such as saline, an ionic fluid that is conductive or another conductive fluid. The irrigating fluid can serve to cool the electrodes 52 of ablation device 50. Irrigated ablation may also create deeper lesions that are more likely to be transmural. In an embodiment, electrodes 52 are composed of an internal metal conductive element covered by a non-metallic conductive fluid or saline eluting porous material that makes electrical contact with the myocardial tissue through the conductive fluid to collect electrograms and to deliver pacing.

Ionic irrigation fluid may also serve to conduct energy. The presence of an ionic fluid layer between one of electrodes 52 and the tissue to be ablated may also improve the likelihood that an ionic fluid layer conforming to the tissue contours is created. In addition to saline, other energy-conducting liquids, such as Ringer's solution, ionic contrast, or even blood, may be used. Diagnostic or therapeutic agents, such as Lidocaine, $Ca^{2+}$ blockers, anti-inflammatory agents, steroids, or gene therapy agents may also be delivered before, with, or after the delivery of the irrigating fluid.

FIG. 3A illustrates a side view of an example of device 50 described in FIG. 2 and FIG. 3B illustrates an end view of the example embodiment of FIG. 3A. In both, bipolar elongate electrodes 52 are positioned on jaws 51 of device 50 and are mechanically squeezing tissue 74 on or near heart 20, such as myocardium with two separate layers 77, 78. Jaws 51 are clamped with a light pressure and are electrically connected with tissue 74. In one example, device 50 can be a parallel or scissors jaw bipolar clamp ablation device. Each one of electrodes 52 may include one discrete conducting member on each jaw 51. This may provide an electrogram measurement of tissue 74 clamped with myocardial conduction vectors 76a, 76b being transverse to the tissue surface orientation, as illustrated in FIG. 3B. The measured bipolar electrogram from sensing module 79 may be a composite of the depolarizations sensed from two separate layers 77, 78 of myocardium 74. The timing of the electrical activity passing through the tissue 74 near jaws 51 is typically separated by at least a few milliseconds, a sharp local electrogram spike potential can be collected by electrodes 52 and displayed on an electrogram recording system. In addition, device 50 can be used for pacing, which can be delivered between the electrodes 52 to determine conduction block. Processor 81 may be operatively coupled to sensing module 79. When sensing module 79 senses characteristics of the electrical activity of heart 20, processor may utilize the information to determine and adequacy of conditions related to ablation of the tissue. These processes will be discussed with respect to FIGS. 6A-6C.

FIG. 4A illustrates a side view of an alternative embodiment of device 50 described in FIG. 2 and FIG. 4B illustrates an end view of the example embodiment of FIG. 4A. Jaws 80 of device 82 each include two elongate electrodes including discrete electrically conducting members 84, 86. This provides the option of collecting the bipolar electrogram from the two side by side elongate electrodes 84, 86 of a single jaw 80 with electrodes 85, 87 on opposing jaw 80 in contact with one surface of the tissue 74. Myocardial electrical conduction vectors 76a, 76b in this case are in line with electrodes 84, 85, 86, 87. A second bipolar electrogram could be collected from electrodes 84, 86 on opposite jaw 80. Like above, the measured bipolar electrogram from sensing module 79 is a composite of the depolarizations sensed from two separate layers 77, 78 of myocardium 74. Also like above, device 82 can be used for pacing, which can be delivered between the two electrode jaws 80 to determine conduction block.

Alternatively, electrodes 84, 85 may be coupled to source of ablation energy 73 and utilized to deliver the ablation energy to create lesion 34 or 36 in tissue 74. Electrodes 86, 87 may be utilized to sense cardiac energy in electrical conduction vectors 76a, 76b to determine entrance block and to deliver pacing energy to determine exit block. By providing the two lateral sets of electrodes 84, 85, 86, 87, device 82 may be positioned once without having to reposition device 82 between the steps ablating tissue and sensing to determine if ablation has been sufficiently performed.

In further alternative embodiments, device 82 may be comprised of three electrodes, for example electrodes 84, 85 and 86. In such an embodiment, ablation electrodes 84 and 85 may deliver ablation energy in a bipolar configuration while electrode 86 may sense and deliver pacing energy in a unipolar configuration. In such a configuration an electrode separate from device 50 may need to be provided to sense and deliver pacing energy. In further alternative embodiments, more than four electrodes 84, 85, 86, 87 may be utilized. For instance, it may be advantageous to have dedicated sensing electrodes and dedicated pacing electrodes.

Alternate embodiments of device 50 are contemplated and the following are just a few of these other embodiments. One example can use parallel or scissors jaw bipolar clamp ablation devices where separate electrodes that are not used for ablation are mounted adjacent and along the length of the jaw-mounted ablation electrodes. These can be on one or both of the jaws. Any bipolar combination of electrodes can be selected to provide an electrogram for evaluation of conduction block or to deliver pacing.

In an embodiment, electrodes 86, 87 may be of equal length to electrodes 84, 85. Electrodes 84, 85, 86, 87 may be positioned in parallel with respect to one another, with electrodes 86, 87 displaced laterally with respect to electrodes 84, 85 so as to remove them from the margin of lesion 34 or 36. In such an embodiment, a user may have the ability to test for conduction block using laterally displaced electrodes 86, 87 without needing to move device 82 from an initial site.

In another example, the ablation device may include a radio frequency (RF) filtered output from the electrogram electrical output from the ablation power supply. This may reduce or eliminate an amount of RF energy that may pass through the electrogram output connection, which may provide a low noise signal for analysis. In still another example, a specially designed or dedicated cable may allow a direct connection of the jaw electrogram output to an electrophysiology recording system, temporary pacer, or programmer/analyzer that can display electrograms, deliver pacing pulses, or both.

Figure 5:
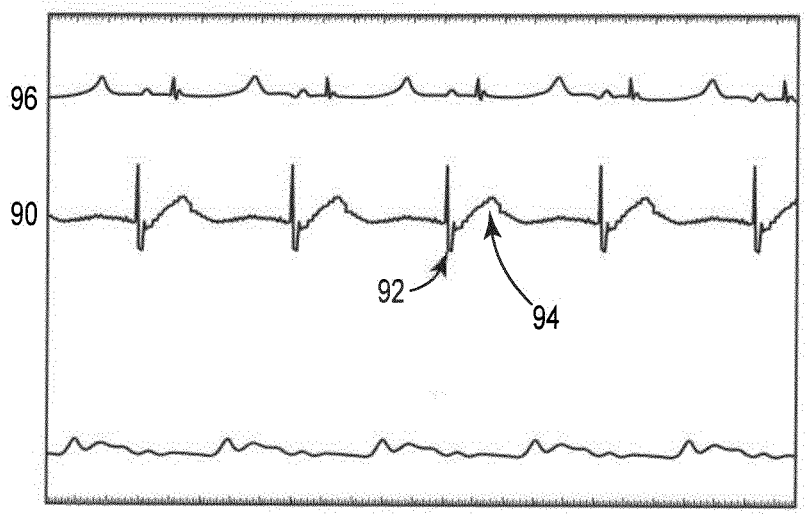
FIG. 5 is an electrogram recording.

FIG. 5 illustrates a typical electrogram recording from signals received from electrodes 52. A bipolar atrial electrogram signal is displayed at 90. The recorded signal 90 shows each local atrial potential 92 followed by a far-field ventricular signal 94. A recorded signal from a surface electrocardiogram (ECG) is shown at 96.

Figure 6A:
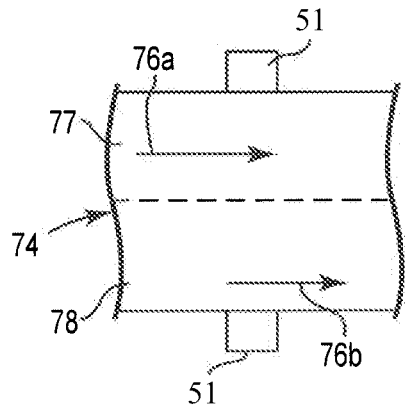
FIGS. 6A, 6B, and 6C illustrate various clamping pressures in the examples of FIGS. 3A and 3B.
Figure 6B:
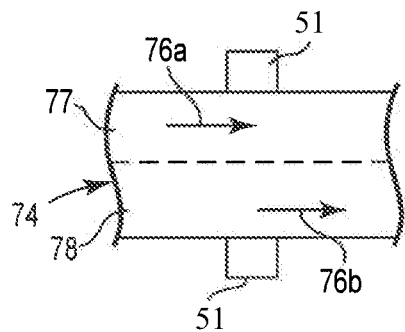
Figure 6C:
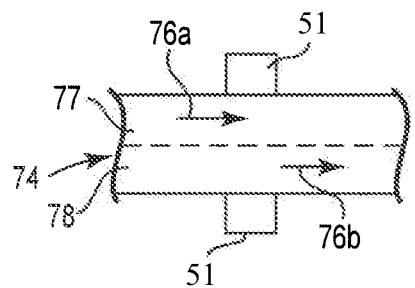

Relative clamping pressure of jaws 51 on the tissue may affect measured electrogram amplitude. FIGS. 6A, 6B, and 6C illustrate end views of the example embodiment of FIG. 3A under different relative clamp pressure from the jaws 51. Vectors 76a, 76b represent direction, timing, amplitude of conduction wavefronts moving in both layers 77, 78 of myocardium 74. FIG. 6A illustrates tissue 74 being subjected to a relatively light electrode jaw pressure and vectors 76a, 76b have a relatively long length representing a high amplitude. FIG. 6B illustrates tissue 74 being subjected to a relatively moderate electrode jaw pressure and vectors 76a, 76b have a relatively smaller length representing a medium amplitude. FIG. 6C illustrates tissue 74 being subjected to a relatively high electrode jaw pressure and vectors 76a, 76b have a relatively short length representing a low amplitude.

In various examples, the clamping force that corresponds to an adequate clamping force for ablation to occur may also correspond to a significant decrease in the amplitude, e.g., voltage amplitude, of the sensed local electrical signals from heart 20. In such embodiments, the local electrogram amplitude may be minimized to the extent possible without causing damage to the tissue. In addition to a significant reduction in electrogram amplitude, the loss of a sharp, local electrogram spike signal that is replaced by a broad, far-field electrogram signal is also indicative of adequate clamping force. In various embodiments, the sensed local electrogram voltage amplitude may be reduced to zero volts. Alternatively, a decrease in amplitude may be sufficient based on a percentage change in amplitude compared between a relatively weak clamping force and a strong clamping force. In an embodiment, if the local electrogram amplitude decreases by at least 75% then the clamping force may be adequate. In another embodiment, if the local electrogram amplitude decreases to about zero, then the clamping force may be adequate. In yet more alternative embodiments, the percentage decrease in clamping force may be alternative values which may be selected based on the condition of the patient.

Figure 7:
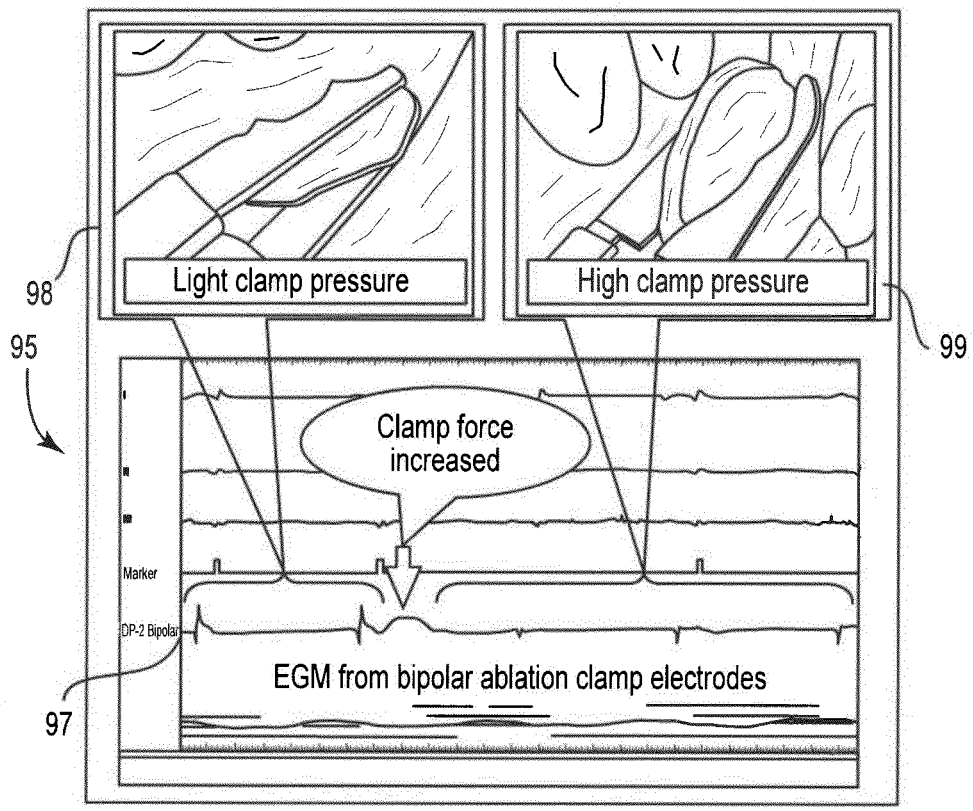
FIG. 7 is another electrogram recording.

FIG. 7 illustrates an embodiment of a user interface 95 that may display to a user electrical characteristics of heart 20 as sensed by sensing module 79. User interface may be coupled to processor 81 to display various data and indicia related to clamp force. As shown on user interface 95, the amplitude of a measured electrogram 97 changes when the jaws are subject to a light clamp pressure 98 as compared with a higher clamp pressure 99. A user may interpret from the displayed electrical activity whether the clamp force is adequate to ablate.

User interface 95 may also be adapted to indicate to a user the adequacy of the clamping force being applied for the purposes of ablation. For instance, if the amplitude of the electrical signals of heart 20 are sufficiently low user interface may display an indicia of the clamp force being acceptable, such as a "+" symbol, a checkmark or a reasonable equivalent. Alternatively, if the amplitude is too high a "−" symbol or reasonable equivalent may be displayed. Alternatively, either a positive or negative result may be described to a user using text to convey the message.

While it may be desirable to exert a relatively strong clamping pressure on the tissue during ablation, it may be desirable to exert a relatively weak clamping pressure during sensing of cardiac signals or delivering pacing energy. In an embodiment, only enough clamp pressure needed to bring the desired length of tissue into contact with the jaws may be preferred to bring about a suitable measurement. As shown above, excessive pressure may reduce an amplitude of sensed signals or may eliminate the electrogram altogether. Because amplitude height of the electrogram may also correlates with clamping pressure, amplitude height can also be used to determine when or whether adequate pressure has been applied to the tissue to be ablated. The greater the clamping force applied, particularly in preparation for and during the delivery of ablation energy, the greater the reduction may be in myocardial activation between jaws 51. Such an activation reduction may be used to assure adequate clamping force prior to and during delivery of ablation energy. Processor 81 and user interface 95 may likewise be adapted to be sensitive to a voltage amplitude or other characteristic which indicates that the clamping force is adequate for sensing and pacing, and may likewise display an indication to a user that the clamping force is adequate.

Measurements of amplitude may differ from the measurements of conduction block, which may emanate from tissue adjacent to the lesion relative to the atria. Other uses are also contemplated. For example, ablation jaws 51 of device 50 may also be useful for the detection of autonomic ganglia. Ablation jaws 51 may deliver high frequency stimulation to the entire line of tissue proximal to and adjacent the lesion line, preferably fat covered, to attempt to elicit an AV nodal or sinus node response. A positive response can indicate the presence of active autonomic ganglia that a surgeon may wish to ablate.

In various embodiments, device 50 and device 82 may incorporate a clamp force regulator that may either show or alert a user as to how much force is being applied on jaws 51 or 80, or may actively prevent excessive force altogether. In an embodiment, the clamp force regulator may be positioned on jaws 51 or 80, or may be coupled to jaws 51 or 80 for a user to see. The clamp force regulator may be a force gauge well known in the art. Alternatively, the clamp force regulator may be a device similar to a torque wrench calibrated to not deliver greater than a certain specified amount of force to jaws 51 or 80. In various embodiments utilizing a torque device, the torque device may be positioned at a junction of jaws 51, 80 in order to prevent excessive clamping force from being exerted on jaws 51, 80 during pacing or sensing activities.

Various circumstances may make various clamping forces to be advantageous. In general, it may be desirable to ablate with between three and eight pounds of force. In various embodiments, it may be desirable to ablate with approximately five pounds of force. For sensing and delivering pacing energy it may be desirable to apply less than five pounds of force. In various embodiments, it may be desirable to sense and pace with as close to zero pounds of force as possible while still maintaining electrical contact with the tissue. In an embodiment it may be desirable to sense and pace with one pound of force. In alternative embodiments, sensing and pacing may be conducted with anywhere from zero to fifteen pounds of force.

Figure 8:
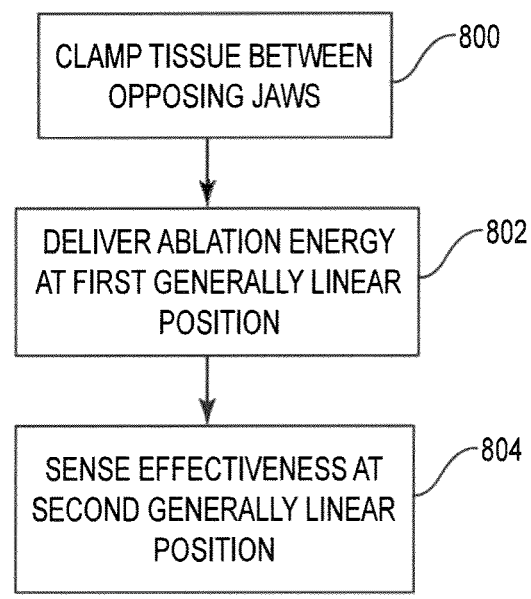
FIG. 8 is a flowchart of a method of utilizing an ablation device.

FIG. 8 is a flowchart of a method for ablating tissue utilizing device 50. Tissue may be clamped (800) between jaws 51 at a first position. Then ablation energy may be delivered (802) at the first generally linear position in order to create lesion 34 or 36. After ablation energy has been delivered, device 50 may then sense (804) an effectiveness of the ablation energy in creating lesion 34 or 36 at a second generally linear position distal of lesion 34 or 36 relative to the atria.

Figure 9:
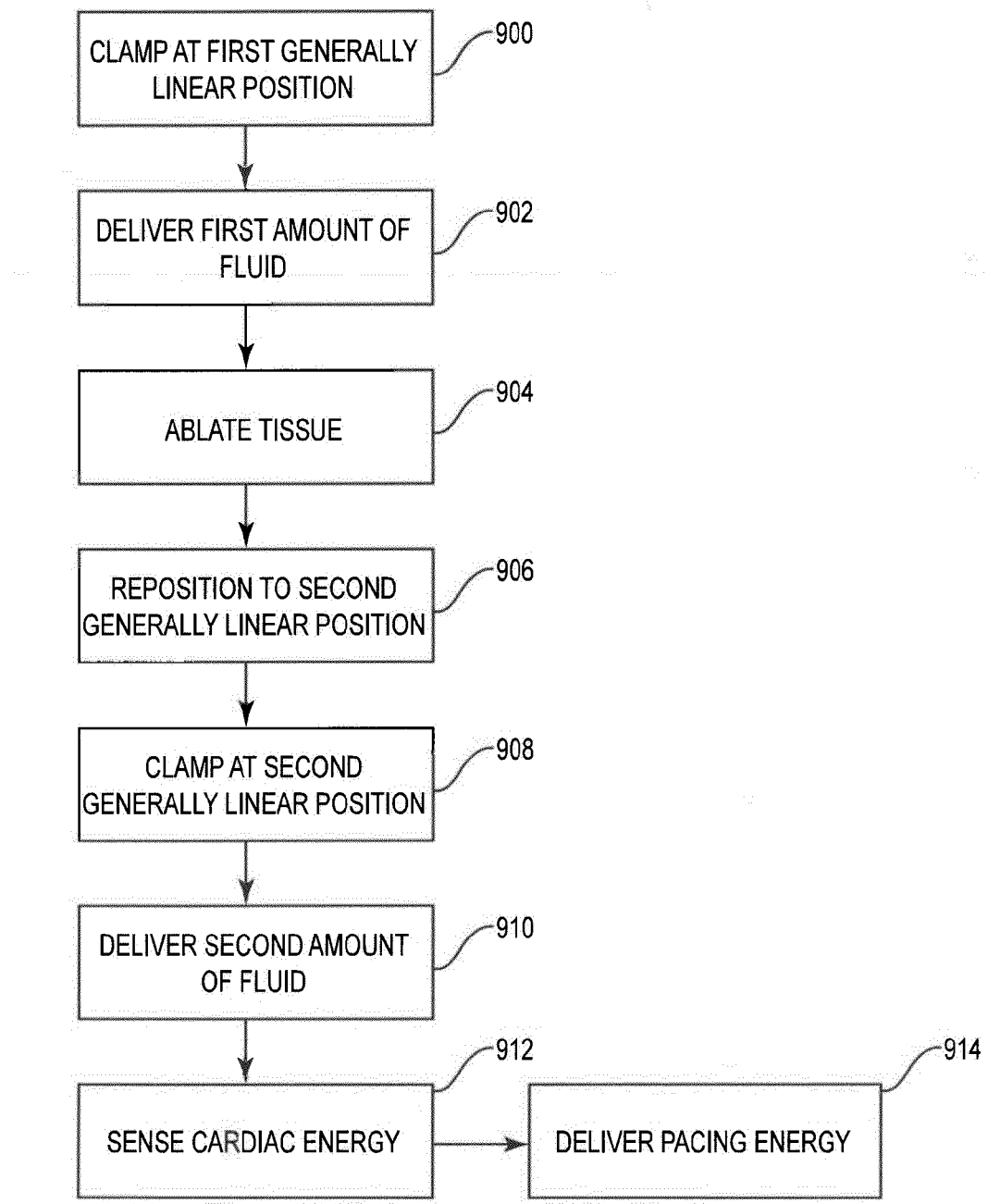
FIG. 9 is a flowchart of a method of utilizing the ablation device of FIGS. 3A and 3B.

FIG. 9 is a flowchart of a method for ablating tissue utilizing device 50. Jaws 51 may be clamped (900) on tissue at a first generally linear position with a first amount of clamping force. A first amount of fluid may be delivered (902) from a source of fluid, and ablation energy may be delivered (904) to the tissue to attempt to create lesion 34 or 36. In various embodiments, fluid may be delivered (902) before during or after ablation energy is delivered (904). In various embodiments, fluid delivery (902) is concurrent with the delivery (904) of ablation energy.

After the delivery of ablation energy (904) device 50 may be repositioned (906) to a second generally linear position distal of lesion 34 or 36 relative to the atria. Jaws 51 may be clamped (908) on the tissue with a second amount of clamping force. In an embodiment, a second amount of fluid (910) may be delivered. In various embodiments it may be unnecessary to deliver a second amount of fluid at all. In other embodiments, the second amount of fluid may be less than the first amount of fluid. In such embodiments, the second amount of fluid may serve to aide an electrical connection between electrodes 52 and the patient tissue, but it may be advantageous to limit the amount of fluid in order to not impede the subsequent measurements.

In various embodiments cardiac activation energy may be sensed (912) in order to determine an effectiveness of the delivery of ablation energy (904) in the creation of lesion 34 or 36. In addition, pacing energy may be delivered (914) and depolarization of cardiac tissue monitored to determine an effectiveness of the delivery of ablation energy (904) in the creation of lesion 34 or 36. In various embodiments, both sensing (912) and pacing (914) may be utilized. In alternative embodiments, one or the other may be utilized. In such embodiments, pacing (914) may not be delivered if cardiac conditions would make depolarization in the heart unlikely or impossible. Such conditions may include atrial fibrillation. Under such conditions it may be desirable to only sense (912). Alternatively, in certain embodiments pacing may be a relatively more effective way of determining the effectiveness of the delivery (904) of ablation energy, and a medical professional may conclude that sensing (912) may not be an efficient use of time. In such an embodiment sensing (912) may be skipped.

Figure 10:
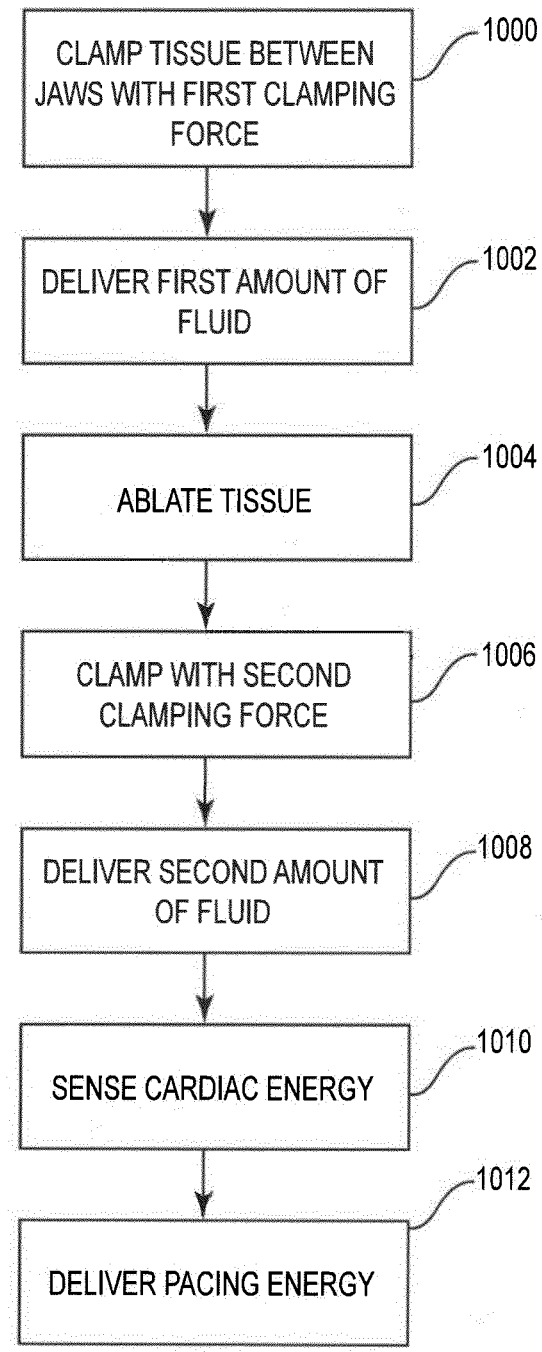
FIG. 10 is a flow chart of a method of utilizing the ablation device of FIGS. 4A and 4B.

FIG. 10 is a flowchart of a method utilizing device 82. The electrodes 84, 85, 86, 87 of device 82 may obviate the need to reposition device 82 as occurred in the method of FIG. 9 (906), as electrodes 84, 85 may be positioned at a first generally linear position to make lesion 34 or 36 while electrodes 86, 87 may already be positioned at the second generally linear position to sense or pace. In particular, jaws 80 may be clamped (1000) with a first clamping force such that electrodes 84, 85 are at the first generally linear position and electrodes 86, 87 are at the second generally linear position distal of said first generally linear position relative to the atria.

A first amount of fluid may be delivered (1002) from a source of fluid, and ablation energy may be delivered (1004) to the tissue to attempt to create lesion 34 or 36. In various embodiments, fluid may be delivered (1002) before during or after ablation energy is delivered (1004). In various embodiments, fluid delivery (1002) is concurrent with the delivery (1004) of ablation energy.

After the delivery of ablation energy (1004) device 82 may be clamped (1006) with a second amount of clamping force. Because electrodes 86, 87 may already be at the second generally linear position it may be unnecessary to reposition device 82. In an embodiment, a second amount of fluid (1008) may be delivered. In various embodiments it may be unnecessary to deliver a second amount of fluid at all. In other embodiments, the second amount of fluid may be less than the first amount of fluid. In such embodiments, the second amount of fluid may serve to aide an electrical connection between electrodes 84, 85, 86, 87 and the patient tissue, but it may be advantageous to limit the amount of fluid in order to not impede the subsequent measurements.

In various embodiments, cardiac energy may be sensed (1010) in order to determine an effectiveness of the delivery of ablation energy (1004) in the creation of lesion 34 or 36. In addition, pacing energy may be delivered (1012) and depolarization of cardiac tissue monitored to determine an effectiveness of the delivery of ablation energy (1004) in the creation of lesion 34 or 36. In various embodiments, both sensing (1010) and pacing (1012) may be utilized. In alternative embodiments, one or the other may be utilized. In such embodiments, pacing (1012) may not be delivered if cardiac conditions would make depolarization in the heart unlikely or impossible. Such conditions may include atrial fibrillation. Under such conditions it may be desirable to only sense (1010). Alternatively, in certain embodiments pacing may be a relatively more effective way of determining the effectiveness of the delivery (1004) of ablation energy, and a medical professional may conclude that sensing (1010) may not be an efficient use of time. In such an embodiment sensing (1010) may be skipped.

Figure 11:
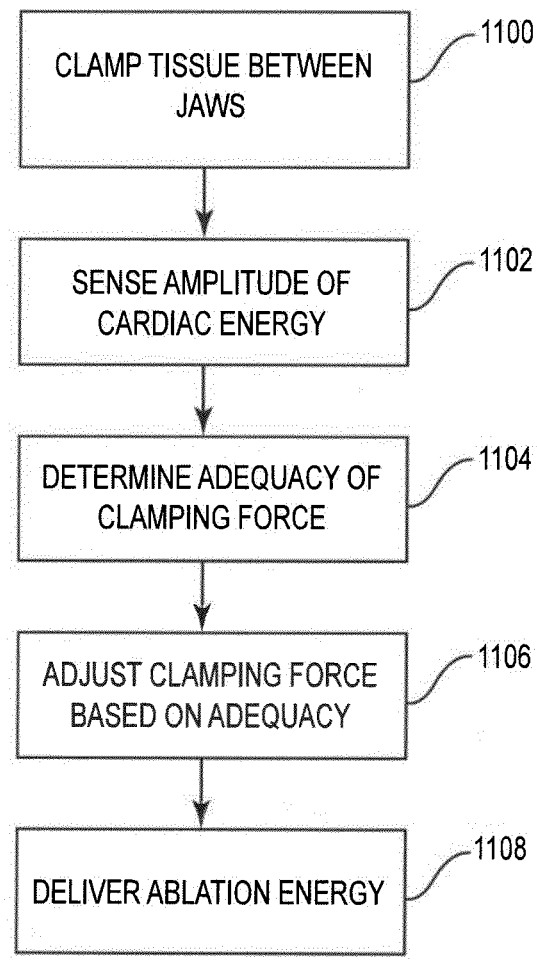
FIG. 11 is a flow chart illustrating using sensed cardiac energy to determine adequacy of clamping force for ablation.

FIG. 11 is a flowchart of a method for determining an adequacy of a clamping force of jaws 51 on tissue. In an embodiment, jaws 51 are clamped (1100) on the tissue and sensing module 79 senses (1102) an amplitude of the electrical signals of heart 20. In alternative embodiments, alternate characteristics may be sensed which indicate electrical conductivity and contractile conductivity of the tissue. In an embodiment, processor 81 may then determine (1104) an adequacy of the clamping force by comparing the sensed amplitude or other characteristic against various requirements or standards. In various embodiments, processor 81 may analyze the amplitude to determine if it has fallen below a minimum value. In an embodiment, the minimum value is about 0.05 mV. In another embodiment, the minimum value is equivalent to the level of signal noise. In yet an alternative embodiment, the minimum value is zero Volts. If the amplitude has fallen below the minimum value then the clamping force may be adequate to ablate the tissue. If the amplitude has not fallen below the minimum value then the clamping force may not be adequate to ablate the tissue.

After the determination (1104) of the adequacy of the clamping force, jaws 51 may be adjusted (1106) by applying a new clamping force depending on the adequacy. In an embodiment, if the minimum value has not been reached, then the clamping force may be increased. In an embodiment, the sensing step (1102) may be repeated. Alternatively, if the clamping force is adequate, then the adjustment step (1106) may be skipped. Ablation energy may be delivered (1108) either based on a determined adequacy of the clamping force or without obtaining an indication of adequacy. In an embodiment, ablation energy is delivered (1108) based on the clamping force being optimized for the tissue.

In various embodiments, the determining step (1104) may be sensitive to the clamping force being too great. In an embodiment, if the sensed amplitude falls below an maximum force threshold then too much clamping force may have been applied. In such an embodiment, user interface 95 may indicate that less clamping force may be applied to obtain an optimized ablation delivery (1108).

In further embodiments, the flow chart of FIG. 11 may be adapted to sensing or pacing. In such an embodiment, determining step (1104) may determine adequacy on the basis of having an adequately high amplitude, and an indication of inadequacy may prompt the adjustment step (1106) to decrease the clamping force. The delivering ablation energy step (1108) may then be a sensing or pacing step, as appropriate.

Although the present invention has been described with reference to preferred embodiments, workers skilled in the art will recognize that changes can be made in form and detail without departing from the spirit and scope of the present invention.

What is claimed is:

1. A method for ablating tissue of a heart having an atrium, comprising:
    clamping the tissue between a pair of opposing jaws;
    ablating a portion of the tissue at a first generally linear position on the tissue by applying ablative energy to two of a plurality of elongate electrodes, each of the two of the plurality of elongate electrodes being coupled in opposing relationship to each other and the pair of opposing jaws, respectively; then
    altering a force applied by the opposing jaws onto the tissue; and
    sensing an effectiveness of ablation on the portion of the tissue at a second generally linear position on the tissue with at least one of the plurality of elongate electrodes positioned on one of the pair of opposing jaws;
    the second linear position on the tissue being laterally distal to the first linear position on the tissue with respect to the atrium,
    wherein the clamping step comprises clamping the tissue between the jaws with a first clamping force, and further comprising clamping the tissue between the jaws with a second clamping force after the ablating step and before the sensing step, wherein the first clamping force is greater than the second clamping force.

2. The method of claim 1, wherein the plurality of elongate electrodes includes a pair of elongate electrodes.

3. The method of claim 2, further comprising repositioning the pair of opposing jaws after the ablating step to the second generally linear position.

4. The method of claim 2, wherein the clamping step comprises clamping the tissue between the jaws with a first clamping force, and further comprises clamping the tissue between the jaws at the second linear position with a second clamping force after the ablating step and before the sensing step, wherein the first clamping force is greater than the second clamping force.

5. The method of claim 1, wherein the plurality of elongate electrodes includes at least three electrodes, and wherein the ablating step ablates with a first two of the plurality of elongate electrodes and the sensing step senses with a third one of the plurality of elongate electrodes.

6. The method of claim 5, wherein the plurality of elongate electrodes are four electrodes;
    wherein the ablating step ablates the tissue with a first two electrodes of the plurality of elongate electrodes; and
    wherein the sensing step senses an effectiveness of ablation with a second two electrodes of the plurality of elongate electrodes, each of the second two of the plurality of elongate electrodes being coupled in opposing relationship to each other and the pair of opposing jaws, respectively.

7. The method of claim 6, wherein the two electrodes of the sensing step are positioned generally parallel to the two electrodes of the ablating step.

8. The method of claim 1, wherein the sensing step includes a first test and a second test.

9. The method of claim 8, wherein the first test senses cardiac energy.

10. The method of claim 9, wherein at least one of the elongate electrodes is coupled to a source of pacing energy and wherein the second test comprises delivering the pacing energy and detecting a response of the heart to the pacing energy.

11. The method of claim 1, wherein the sensing step senses using two of the plurality of electrodes.

12. The method of claim 1, wherein the heart has a right pulmonary vein having a width and a left pulmonary vein having a width, and wherein the first generally linear position spans the width of at least one of the right pulmonary vein and the left pulmonary vein.

13. The method of claim 12, wherein the second generally linear position spans a width of the at least one of the right pulmonary vein and the left pulmonary vein distal of the first generally linear position relative to the atrium.

14. A method for ablating tissue of a heart having an atrium, comprising:
    clamping the tissue between a pair of opposing jaws;
    ablating a portion of the tissue at a first generally linear position on the tissue by applying ablative energy to two of a plurality of elongate electrodes, each of the two of the plurality of elongate electrodes being coupled in opposing relationship to each other and the pair of opposing jaws, respectively; then
    altering a force applied by the opposing jaws onto the tissue; and
    sensing an effectiveness of ablation on the portion of the tissue at a second generally linear position on the tissue with at least one of the plurality of elongate electrodes positioned on one of the pair of opposing jaws;
    the second linear position on the tissue being laterally distal to the first linear position on the tissue with respect to the atrium,
    wherein the jaws are fluidly coupled to a fluid supply of a fluid, and wherein during the ablating step a first amount of the fluid is delivered to the jaws, and wherein during the sensing step a second amount of the fluid is delivered to the jaws, the first amount of fluid being greater than the second amount of fluid.

15. The method of claim 14, wherein the first amount and the second amount are a first total volume of the fluid and a second total volume of the fluid, respectively.

16. The method of claim 14, wherein the first amount and the second amount are delivered at a first rate of delivery of the fluid and a second rate of delivery of the fluid, respectively.

* * * * *